US011484557B2

(12) United States Patent
Paek et al.

(10) Patent No.: US 11,484,557 B2
(45) Date of Patent: Nov. 1, 2022

(54) **HUMAN-DERIVED *LACTOBACILLUS FERMENTUM* MG4231 OR *LACTOBACILLUS FERMENTUM* MG4244 STRAIN HAVING ANTI-OBESITY ACTIVITY, AND COMPOSITION COMPRISING SAME**

(71) Applicant: MEDIOGEN CO., LTD., Chungcheongbuk-do (KR)

(72) Inventors: Nam Soo Paek, Seoul (KR); Chang Ho Kang, Chungcheongbuk-do (KR)

(73) Assignee: Mediogen Co., Ltd., Chungcheongbuk-do (KR)

( * ) Notice: Subject to any disclaimer, the term of this patent is extended or adjusted under 35 U.S.C. 154(b) by 0 days.

(21) Appl. No.: 17/271,076

(22) PCT Filed: Aug. 27, 2019

(86) PCT No.: PCT/KR2019/010961
§ 371 (c)(1),
(2) Date: Feb. 24, 2021

(87) PCT Pub. No.: WO2020/045971
PCT Pub. Date: Mar. 5, 2020

(65) Prior Publication Data
US 2021/0322493 A1    Oct. 21, 2021

(30) Foreign Application Priority Data

Aug. 31, 2018    (KR) .................. 10-2018-0103506

(51) Int. Cl.
*A61K 39/02* (2006.01)
*A61K 35/747* (2015.01)
*A23L 33/135* (2016.01)
*C12N 1/20* (2006.01)
*C12R 1/225* (2006.01)

(52) U.S. Cl.
CPC .......... *A61K 35/747* (2013.01); *A23L 33/135* (2016.08); *C12N 1/20* (2013.01); *C12R 2001/225* (2021.05)

(58) Field of Classification Search
None
See application file for complete search history.

(56) References Cited

U.S. PATENT DOCUMENTS

2015/0343003 A1* 12/2015 Kullisaar ................ A61P 39/06
424/456

FOREIGN PATENT DOCUMENTS

| KR | 20010106068 A | 11/2001 |
| KR | 20050010451 A | 1/2005 |
| KR | 20090113478 A | 11/2009 |
| KR | 20150098202 A | 8/2015 |
| KR | 20170119099 A | 10/2017 |
| KR | 101981333 B1 | 5/2019 |

OTHER PUBLICATIONS

"International Search Report corresponding to International Application No. PCT/KR2019/010961 dated Dec. 27, 2019".
Dahiya, Dinesh K, et al., "Conjugated linoleic acid enriched skim milk prepared with Lactobacillus fermentum DDHI27 endorsed antiobesity in mice", Future Microbiology 13(9):1-14 (Apr. 10, 2018).
Dahiya, Dinesh Kumar, et al., "Evaluation of Survival, Free Radical Scavenging and Human Enterocyte Adherence Potential of Lactobacilli with Anti-Obesity and Anti-Inflammatory CLA Isomer-Producing Attributes", Journal or Food Processing and Preservation 39:2866-2877 (2015).
Yoo, Sae-Rom , et al., "Probiotics L. Plantarum and L. Curvatus in Combination Alter Hepatic Lipid Metabolism and Suppress Diet-Induced Obesity", Obesity 21:2571-2578 (2013).
Kang, Chang-Ho , et al., "In vitro Probiotic Evaluation of Potential Antiobesity Lactic Acid Bacteria Isolated from Human Vagina and Shellfish", Korean Society for Biotechnology and Bioengineering Journal 33(3):161-167 (Aug. 13, 2018).
Park, Do-Young , et al., "The Inhibitory Effect of Lactobacillus plantarum KY1032 Cell Extract on the Adipogenesis of 3T3-L1 Cells", Journal of Medicinal Food 14(6):670-675 (Feb. 15, 2011).

* cited by examiner

*Primary Examiner* — Jennifer E Graser
(74) *Attorney, Agent, or Firm* — Myers Bigel, P.A.

(57) ABSTRACT

The present invention relates to: human-derived *Lactobacillus fermentum* MG4231 or *Lactobacillus fermentum* MG4244; and a pharmaceutical composition, a food composition, a quasi-drug composition and a health functional food for preventing or treating obesity-related diseases, all of which include the same as an active ingredient. A *Lactobacillus fermentum* MG4231 strain or MG4244 strain of the present invention exhibits an anti-obesity activity for inhibiting a lipase enzyme activity, inhibiting preadipocyte differentiation and inhibiting triglyceride accumulation, has an excellent ability to form colonies on the epithelial cells of a digestive tract by means of an excellent auto-aggregation ability, and has resistance to acid and bile, thereby being variously usable as a pharmaceutical composition, a food composition, a quasi-drug composition and a health functional food for the purpose of treating and preventing obesity-related diseases.

6 Claims, 4 Drawing Sheets

HUMAN-DERIVED *LACTOBACILLUS FERMENTUM* MG4231 OR *LACTOBACILLUS FERMENTUM* MG4244 STRAIN HAVING ANTI-OBESITY ACTIVITY, AND COMPOSITION COMPRISING SAME

RELATED APPLICATIONS

This application is a 35 U.S.C. § 371 national phase application of PCT Application PCT/KR2019/010961 filed Aug. 27, 2019, which claims priority to Korean Application No. 10-2018-0103506 filed Aug. 31, 2018. The entire contents of each are incorporated herein by reference in its entirety.

FIELD OF THE INVENTION

The present disclosure relates to human-derived *Lactobacillus fermentum* MG4231 or *Lactobacillus fermentum* MG4244 and pharmaceutical composition and food composition, quasi-drug composition and health functional food for preventing or treating obesity-related diseases using the same as an active ingredient.

BACKGROUND OF THE INVENTION

Lactic acid bacteria have a special physiological activity, and are generally regarded as safe bacteria. Lactic acid bacteria are not only used in the production of various fermented foods, but also are widely used in dairy products and fermented fruit products with functional and probiotic properties. Recently, as consumers' demand for natural supplements to replace chemical supplements increases, the Lactic acid bacteria has emerged as an alternative thereto. Probiotics are living microorganisms that have a very beneficial effect on the health of the host animal, and improve the balance of intestinal microorganisms and increase the absorption of nutrients. Further, probiotics have the property of showing the antibacterial action of pathogenic microorganisms in the intestinal environment. Although various microorganisms are contained in probiotics, the genus *Lactobacillus* and the genus *Bifidobacterium* occupy the most contents thereof. In particular, the genus *Lactobacillus* is generally used in the fermentation process of dairy products, meat, fruits and vegetables and cereal products.

Obesity is known to be a major cause of heart disease, cancer, arthritis, and diabetes. Despite increasing public awareness to solve obesity, the number of obesity patients is constantly increasing. Obesity occurs as the number of adipocytes increases as a result of adipogenesis and the lipid content of adipocytes increases. The adipocyte plays a major role in synthesizing and storing excess calories into triglycerides. As a result of adipogenesis, a size and the number of adipocytes increase and intracellular lipid accumulation is accelerated.

In the past, adipose tissue was thought only as an energy storage organ that stores excess energy in the form of triglycerol and releases the same when needed. Recently, adipose tissue has been regarded as an important endocrine organ which secretes various adipokines such as adiponectin, leptin, and resistin, and thus regulates homeostasis of energy (Trends Endocrinol Metab 13:18, 2002). Therefore, understanding the proliferation of adipocytes and substances secreted from adipocytes, and the understanding of in vivo regulatory mechanisms thereof are considered to be the foundation for understanding obesity and various diseases resulting therefrom and developing effective therapeutic agents therefor. Accordingly, research on the regulation of adipocyte differentiation is being actively conducted. In relation to causes of increase in adipocytes in obesity patients, a main mechanism of the increase includes differentiation from preadipocytes in the body. The process of differentiation of preadipocytes into adipocytes has been studied using cells such as 3T3-L1. Several types of transcription factors, particularly, transcription factors known to be involved in formation of adipocytes, C/EBPs (CAAT enhancer binding proteins), PPARs (Peroxisome Proliferator Activated receptor), ADD/SREBPs (Adipocyte determination and differentiation dependent factor 1/sterol response element binding proteins), and the like are expressed over time and regulate the process (Bart A Jessen et al., Gene, 299, pp 95-100, 2002; Darlington et al., J. Biol. Chem., 273, pp 30057-30060, 1998; Brun R P et al., Curr. Opin. Cell. Biol., 8, pp 826-832, 1996). When stimulation of hormones such as MDI (isobutylmethylxanthin, dexamethasone and insulin) occurs, C/EBP β and δ are first and temporarily expressed, and initiate differentiation into adipocytes (Reusch J. E et al., Mol. Cell. Biol., 20, pp 1008-1020, 2000). Only adipocytes that have completed the differentiation process synthesize fatty acids and store triglycerides. Therefore, current research trends are focused on searching for substances that may inhibit metabolic processes related to adipocyte differentiation for preventing or treating obesity-related metabolic diseases. That is, attempts to treat obesity are being made via adipocyte regulation based on the mechanism of formation of obesity. This is intended to reduce the amount of fat by inhibiting fat synthesis or promoting fat decomposition and oxidation, and to reduce adipocyte count by inhibiting adipocyte differentiation. Transcription factors, proteins and adipocyte secreting substances (adipokines) as known to mediate or regulate these processes are emerging as a target for the development of new obesity treatment agents. The obesity treatment agents known to date include Xenical (Roche Pharmaceuticals, Switzerland), Reductil (Ebot, USA), and Exolise (Atopharma, France), and are classified into appetite inhibitors, energy consumption accelerators, and fat absorption inhibitor. Most obesity treatment agents are appetite inhibitors that inhibit appetite by regulating neurotransmitters related to the hypothalamus.

However, the conventional obesity treatment agents have side effects such as cardiac disease, respiratory disease, nervous system disease, and the like, and the persistence of their efficacy is low. Therefore, it is necessary to develop further improved obesity treatment agents. Further, there are few therapeutic agents that have a satisfactory therapeutic effect without side effects even, among the products currently being developed. The development of a new obesity treatment agent is required.

Further, many efforts have been made to reduce blood cholesterol levels by using lactic acid bacteria, which have been regarded as safe microorganisms. Lactic acid bacteria have been reported to exhibit effects such as maintenance of normal intestinal flora, amelioration of intestinal flora, inhibition of carcinogenesis, inhibition of colitis, and non-specific activity of the host's immune system. Among them, *Lactobacillus* genus strain is a major member of the normal microbial cluster living in the human intestine, and has long been known as important for maintaining a healthy digestive system and vaginal environment. According to the U.S. Public Health Service guidelines, all *Lactobacillus* strains currently deposited on the U.S. strain depository organization (ATCC) are classified as Bio-safety Level 1' having no known potential risk of causing disease to humans or animals. However, lactic acid bacteria are known to have excellent immune response modulating effects, anticancer and antioxidant effects based on previous studies. However, studies on the adipogenesis inhibition effect and fat accumulation inhibition effect of *Lactobacillus* strain are insufficient.

DISCLOSURE

Technical Purpose

Therefore, the present inventors were conducting a study on the adipogenesis inhibition effect and fat accumulation inhibition effect of *Lactobacillus* strain, and thus have identified that human-derived *Lactobacillus fermentum* MG4231 and MG4244 have anti-obesity activity. Thus, the present disclosure was completed.

Therefore, a purpose of the present disclosure is to provide human-derived isolated *Lactobacillus fermentum* MG4231 or *Lactobacillus fermentum* MG4244, and a pharmaceutical composition and a food composition, a quasi-drug composition and a health functional food for preventing or treating obesity-related diseases, the composition containing the human-derived isolated *Lactobacillus fermentum* MG4231 or *Lactobacillus fermentum* MG4244 as an active ingredient.

Technical Solution

To achieve the purpose, the present disclosure provides a human-derived *Lactobacillus fermentum* MG4231 strain (deposition number: KCTC 13593BP) or *Lactobacillus fermentum* MG4244 (deposition number: KCTC 13594BP) strain.

Further, the present disclosure provides a pharmaceutical composition for preventing or treating obesity-related diseases, the composition containing the strain.

Further, the present disclosure provides a food composition for preventing or ameliorating obesity-related diseases, the composition containing the strain.

Further, the present disclosure provides a health functional food for preventing or ameliorating obesity-related diseases, the composition containing the strain.

Further, the present disclosure provides a quasi-drug composition for preventing or ameliorating obesity-related diseases, the composition containing the strain.

Advantageous Effects

The *Lactobacillus fermentum* strain MG4231 or strain MG4244 according to the present disclosure exhibits anti-obesity activity via inhibition of lipase enzyme activity, inhibition of preadipocyte differentiation, and inhibition of triglyceride accumulation, and has excellent colony formation ability in epithelial cells of a digestive tract via excellent auto-aggregation ability, and has resistance to acidity and bile. Thus, the *Lactobacillus fermentum* strain MG4231 or strain MG4244 according to the present disclosure may be used in various ways for a pharmaceutical composition, a food composition or a quasi-drug composition and a health functional food for the purpose of treatment and prevention of obesity-related diseases.

MODES OF THE INVENTION

The present disclosure provides a human-derived *Lactobacillus fermentum* MG4231 strain (deposition number: KCTC 13593BP) or *Lactobacillus fermentum* MG4244 (deposition number: KCTC 13594BP) strain.

Hereinafter, the present disclosure will be described in more detail.

The *Lactobacillus fermentum* MG4231 strain or *Lactobacillus fermentum* MG4244 strain is a novel strain having anti-obesity effects. In the present disclosure, the term "*Lactobacillus*" refers to a bacterium that produces a large amount of lactic acid by fermenting saccharides widely distributed in nature to obtain energy. *Lactobacillus* is a Gram-positive, spore-free bacilli and exhibits polymorphism. Microorganisms belonging to the genus *Lactobacillus* include *Lactobacillus fermentum* (*L. fermentum*), *Lactobacillus plantarum* (*L. plantarum*), *Lactobacillus brevis* (*L. brevis*), and the like. The present inventors identified *Lactobacillus fermentum* MG4231 strain or *Lactobacillus fermentum* MG4244 strain having inhibition of lipase enzyme activity, inhibition of preadipocyte differentiation, or triglyceride accumulation inhibition activity as follows.

In order to separate the *Lactobacillus* strain according to the present disclosure, the strain was isolated from the vagina of healthy Korean women. Numerous lactic acid bacteria exist in a healthy vagina, and their distribution is known to vary according to race, age, and environment. Among the separated strains, two strains having the best anti-obesity activity were selected and identified as *Lactobacillus fermentum*. One of the two strains was named *Lactobacillus fermentum* MG4231 and deposited on the Korea Microbial Conservation Center to receive accession number KCTC 13593BP. The other of the two strains was named *Lactobacillus fermentum* MG4244 and deposited on the Korea Microbial Conservation Center to receive the accession number KCTC 13594BP.

In an example of the present disclosure, the novel isolated *Lactobacillus fermentum* MG4231 strain or *Lactobacillus fermentum* MG4244 strain was specifically identified as having an excellent anti-obesity effect.

The *Lactobacillus fermentum* MG4231 strain or the *Lactobacillus fermentum* MG4244 strain is characterized by having at least one activity selected from a group consisting of inhibition of lipase enzyme activity, inhibition of preadipocyte differentiation, and inhibition of triglyceride accumulation.

Further, the strain is characterized by having acid resistance and bile resistance. In an example of the present disclosure, it was identified that the *Lactobacillus fermen-*

*tum* MG4231 strain or the *Lactobacillus fermentum* MG4244 strain maintains a high viability in pH 2 to 4 as a strong acid condition containing pepsin. Further, in an example of the present disclosure, it was identified that the *Lactobacillus fermentum* MG4231 strain or the *Lactobacillus fermentum* MG4244 strain maintains a high viability in bile containing pancreatin under the conditions of pH 7 and pH 8.

*Lactobacillus fermentum* MG4231 strain or *Lactobacillus fermentum* MG4244 strain according to the present disclosure exhibits excellent auto-aggregation ability, thereby preventing the removal of probiotics by intestinal spasm and effectively forming colonies in the epithelial cells of the digestive tract in the intestine.

Further, the present disclosure provides a pharmaceutical composition for preventing or treating obesity-related diseases, the composition containing the strain.

The pharmaceutical composition contains *Lactobacillus fermentum* MG4231 strain or *Lactobacillus fermentum* MG4244 strain according to the present disclosure as an active ingredient. The strain is preferably contained in an amount of 0.01 to 95 parts by weight, more preferably, 1 to 80 parts by weight, based on a total of 100 parts by weight of the pharmaceutical composition. When the content is lower than 0.01 parts by weight, the dosage efficiency may decrease. When the content exceeds 95 parts by weight, there may be difficulties in formulation of the pharmaceutical composition.

The pharmaceutical composition containing *Lactobacillus fermentum* MG4231 strain or *Lactobacillus fermentum* MG4244 strain as an active ingredient according to the present disclosure may be used directly as a composition itself or an adjuvant that has the effect of preventing, ameliorating or treating obesity-related diseases via inhibition of lipase enzyme activity, inhibition of preadipocyte differentiation, or triglyceride accumulation inhibition.

The pharmaceutical composition according to the present disclosure may contain a pharmaceutical effective amount of *Lactobacillus fermentum* MG4231 strain or *Lactobacillus fermentum* MG4244 strain alone or in combination with at least one pharmaceutical acceptable carrier, excipient or diluent. The term "pharmaceutically effective amount" refers to an amount sufficient to prevent, ameliorate or treat the obesity-related diseases via inhibition of lipase enzyme activity, inhibition of preadipocyte differentiation, or triglyceride accumulation inhibition. The "pharmaceutically acceptable matter" refers to a matter that is physiologically acceptable and does not usually cause allergic reactions such as gastrointestinal disorders, dizziness or similar reactions when administered to humans.

Further, the pharmaceutical composition according to the present disclosure is formulated in the form of oral dosage forms such as powders, granules, tablets, capsules, suspensions, emulsions, syrups and aerosols, external preparations, suppositories and sterile injectable solutions according to conventional methods. Suitable formulations known in the art are preferably those disclosed in Remington's Pharmaceutical Science, recently, Mack Publishing Company, Easton Pa. Carriers, excipients and diluents that may be contained therein include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, and the like. When formulating the pharmaceutical composition, the formulation may be prepared using diluents or excipients such as commonly used fillers, extenders, binders, wetting agents, disintegrants, and surfactants. Solid preparations for oral administration include tablets, pills, powders, granules, capsules, etc. These solid preparations are prepared by mixing at least one excipient, such as starch, calcium carbonate, sucrose, lactose, or gelatin with the composition. Further, in addition to simple excipients, lubricants such as magnesium stearate and talc may be used. Liquid preparations for oral use include suspensions, liquid solutions, emulsions, syrups, etc. However, in addition to water as a simple diluent commonly used, and liquid paraffin, various excipients, for example, wetting agents, sweetening agents, fragrances, preservatives, and the like may be contained therein. Preparations for parenteral administration include sterile aqueous solutions, non-aqueous solutions, suspensions, emulsions, lyophilized preparations, suppositories, and the like. The non-aqueous solution and suspensions may include propylene glycol, polyethylene glycol, vegetable oil such as olive oil, and injectable ester such as ethyl oleate. A base for suppositories may include witepsol, macrogol, tween 61, cacao butter, laurin, glycerogelatin, and the like.

The pharmaceutical composition according to the present disclosure may be administered in the amount of an active ingredient or pharmaceutical composition that induces a biological or medical response in a tissue system, animal or human, as conceived by a researcher, veterinarian, physician or other clinicians, that is, in a therapeutically effective amount which alleviates the symptom of the disease or disorder being treated. It is obvious to those skilled in the art that the therapeutically effective dosage and frequency of administration for the pharmaceutical composition according to the present disclosure will vary according to the desired effect. Therefore, the optimal dosage to be administered may be easily determined by a person skilled in the art, and may vary based on various factors including a type of disease, severity of disease, content of active ingredients and other ingredients contained in the composition, a type of formulation, and age, weight, general health status, sex and diet of a patient, administration time, route of administration and secretion rate of composition, the duration of treatment, and concurrently used drugs. For a desirable effect, the pharmaceutical composition according to the present disclosure may be administered in an amount of 1 to 10,000 mg/kg/day, preferably 1 to 200 mg/kg/day, and may be administered once a day, or may be administered several times in a divided manner.

The pharmaceutical composition according to the present disclosure may be administered to the subject via various routes. Any route of administration may be considered. For example, the pharmaceutical composition according to the present disclosure may be administered to the subject via oral, rectal, or intravenous, intramuscular, subcutaneous, intrauterine dura mater or cerebrovascular route injection.

The content of *Lactobacillus fermentum* MG4231 strain or *Lactobacillus fermentum* MG4244 strain in the pharmaceutical composition according to the present disclosure may be appropriately selected depending on the degree of absorption and excretion rate of the active ingredient in the body, and age, sex and condition of the subject.

The pharmaceutical composition according to the present disclosure may be used alone, but may be used in combination with other appropriate treatment methods (e.g., surgery, radiation therapy, hormone therapy, chemotherapy, and a method of using a biological reaction modifier, etc.) that are usually effective for enhancing treatment of obesity-related diseases according to the choice of a skilled person to the art.

The obesity-related disease according to the present disclosure may be one or more selected from a group consisting of fatty liver, type 2 diabetes, hyperlipidemia, cardiovascular disease, arteriosclerosis and lipid-related metabolic syndrome. However, the disclosure is not limited thereto.

In the present disclosure, the term "prevention" may mean any action that inhibits or delays the onset of obesity-related diseases by administering the composition according to the present disclosure to a subject to prevent or treat obesity-related diseases.

In the present disclosure, the term "treatment" may refer to any action in which the composition according to the present disclosure is administered to a subject suspected of having an obesity-related disease to reduce the symptoms of the obesity-related disease.

In the present disclosure, the term "amelioration" may refer to any action that at least reduces a parameter related to the condition being treated, for example, a degree of the symptom.

In the present disclosure, the term "subject" may refer to any animal including humans, who have or are likely to have obesity-related diseases.

Further, the present disclosure provides a food composition for prevention or amelioration of obesity-related diseases, the composition containing the strain.

In the food composition according to the present disclosure, a kind of the food is not particularly limited. The food may include all food in the usual sense. Non-limiting examples of foods to which the present composition may be added include meat, sausage, bread, chocolate, candy, snacks, confectionery, pizza, ramen, other noodles, gum, dairy products containing ice cream, various soups, beverages, tea, drinks, alcoholic beverages, and vitamin complexes. When using the composition as a food additive, the composition may be directly added to the food or may be used in combination with other foods or food ingredients. The composition may be suitably used according to a conventional method.

In the present specification, the term food refers to a natural product or processed product containing one or more nutrients. Preferably, the food may be subjected to a certain processing and thus may be ready to be eaten directly. The food composition is a conventional one and intended to include all of food, food additives, health functional foods and beverages.

Non-limiting examples of foods to which the present composition may be added may include, for example, various foods, beverages, gum, candy, tea, vitamin complexes, and functional foods. Additionally, in the present disclosure, the foods may include special nutritional foods (e.g., formulas, infants, baby foods, etc.), processed meat products, fish products, tofu, jelly, noodles (e.g., ramen, noodle, etc.), health supplement food, seasoned foods (e.g. soy sauce, miso, red pepper paste, mixed sauce, etc.), sauces, confectionery (e.g., snacks), dairy products (e.g. fermented milk, cheese, etc.), other processed foods, kimchi, pickled food (various kimchi, pickles, etc.), drinks (e.g. fruits, vegetable drinks, soy milk, fermented drinks, ice cream, etc.), natural seasonings (e.g., ramen soup, etc.), vitamin complexes, alcoholic beverages, and other health supplement foods. However, the present disclosure is not limited thereto. The food, beverage or food additives may be prepared by conventional preparation methods.

In particular, the present inventors have identified that *Lactobacillus fermentum* MG4231 strain or *Lactobacillus fermentum* MG4244 strain may prevent, treat, or alleviate obesity-related diseases via inhibition of lipase enzyme activity, inhibition of preadipocyte differentiation, or triglyceride accumulation inhibition. Thus, the food composition containing *Lactobacillus fermentum* MG4231 strain or *Lactobacillus fermentum* MG4244 strain may be used directly for any food including fermented foods.

Further, the present disclosure provides a health functional food for prevention or amelioration of obesity-related diseases, the composition containing the strain.

In the present disclosure, the term "health functional food" refers to a food made of specific ingredients as raw materials or manufactured and processed by extracting, concentrating, refining, and mixing specific ingredients contained in food materials for the purpose of health supplementation, or refers to a food that is designed and processed to allow bioregulatory functions of a food composition, such as bio-defense, biorhythm control, disease prevention and disease recovery to be sufficiently realized in the body, which may perform functions related to the disease prevention, the disease recovery, or the like.

When using the *Lactobacillus fermentum* MG4231 strain or the *Lactobacillus fermentum* MG4244 strain according to the present disclosure for the health functional food, the *Lactobacillus fermentum* MG4231 strain or the *Lactobacillus fermentum* MG4244 strain may be directly added to the food or may be used in combination with other foods or food ingredients. The former or latter manner may be appropriately selected based on needs. Further, an amount of the *Lactobacillus fermentum* MG4231 strain or *Lactobacillus fermentum* MG4244 strain to be added may be appropriately determined according to the purpose of use. The *Lactobacillus fermentum* MG4231 strain or *Lactobacillus fermentum* MG4244 strain according to the present disclosure may have biosafety and exhibit an effect of increasing the activity in proportion to a concentration thereof. Thus, it is obvious that the *Lactobacillus fermentum* MG4231 strain or *Lactobacillus fermentum* MG4244 strain according to the present disclosure may be used in an appropriate amount without being limited to a specific range.

Further, according to the present disclosure, there is no particular limitation on the types of health functional foods to which the *Lactobacillus fermentum* MG4231 strain or the *Lactobacillus fermentum* MG4244 strain may be added. For example, health functional foods may include ramen, other noodles, beverages, tea, drinks, alcoholic beverages, various soups, meats, sausages, bread, chocolate, candy, confectionery, pizza, gum, dairy products including ice cream, or vitamin complexes. In particular, *Lactobacillus fermentum* MG901 or *Lactobacillus plantarum* MG989 according to the present disclosure has the effect of increased viability against gastric acid or bile acid in the digestive tract, increased intracellular adhesion, and inhibition of lipase enzyme activity, inhibition of preadipocyte differentiation or inhibition of triglyceride accumulation and thus is excellent in preventing, alleviating or treating obesity-related diseases, and thus may be particularly suitable for producing fermented milk or fermented products with various lactic acid bacteria. Examples of the fermented milk health functional food may include, for example, yogurt, calpis, cheese, butter, etc. Fermented products may include tofu, soybean paste, fermented soybeans, jelly, and kimchi. The fermented milk or fermented product may be easily produced by replacing only the strain with *Lactobacillus fermentum* MG4231 strain or *Lactobacillus fermentum* MG4244 strain according to the present disclosure in a conventional production method.

Further, the *Lactobacillus fermentum* MG4231 strain or *Lactobacillus fermentum* MG4244 strain according to the present disclosure may be mixed with suitable other auxiliary ingredients or known additives that may be contained in a health functional food conventionally according to the choice of a skilled person. The known additives may include other microorganisms that may be used in combination with the strain according to the present disclosure.

Further, the present disclosure provides a quasi-drug composition for prevention or amelioration of obesity-related diseases, the composition containing the strain.

The strain according to the present disclosure may be added to the quasi-drug composition for the purpose of preventing or ameliorating obesity-related diseases. When using *Lactobacillus fermentum* MG4231 strain or *Lactobacillus fermentum* MG4244 strain according to the present disclosure as a quasi-drug additive, the strain may be added directly thereto or may be used in combination with other quasi-drug ingredients, and may be suitably used according to a conventional method. An amount of the active ingredient may be appropriately determined according to the purpose of use (prevention, health or therapeutic treatment).

Hereinafter, in order to help understanding of the present disclosure, preferable examples and formulation examples are presented. However, the following examples and formulation examples are provided only to allow the skilled person to the art to more easily understand the present disclosure, and thus the content according to the present disclosure is not limited thereto.

Example 1. Separation of Strain to be Used and Preparation of Sample to be Used A sample was collected from the inner wall of the vagina of a healthy woman with a cotton swab at the Department of Obstetrics and Gynecology at Mokdong Hospital, Ewha Womans University and transported to the laboratory in a refrigerated state. The kit containing the sample collected with the cotton swab was immediately spread on Rogosa SL (Difco, USA) medium and incubated at 37° C. for 48 hours in an anaerobic condition. When colonies were formed in the medium, each colony was smeared on Rogosa SL medium and purely isolated colonies were finally selected via Gram staining (positive), morphological (*bacillus*) observation, and biochemical characteristics (catalase negative). The final strain stored in a frozen state in 10% (v/v) glycerol at −70° C. was used in the following example.

After the strain was cultured at 37° C. for 18 hours, the culture solution was centrifuged at 4° C. at 1,100×g for 3 minutes, and then washed twice with phosphate-buffer saline (PBS, pH7). The washed lactic acid strain was lyophilized and resuspended in PBS at a concentration of 10 mg/mL, and then homogenized using a sonicator (VCX 400, Sonics & Materials Inc., CT, USA). The homogenized lactic acid strain was centrifuged at 1,100×g at 4° C. for 15 minutes, and then used as a sample in following Example.

Example 2. Identification of Strain with Obesity Prevention and Treatment Effect 2.1 Identification of Strains Having Inhibition Ability of Lipase Enzyme Activity In order to select a strain with excellent obesity prevention and treatment effect among the 221 strains as obtained in Example 1, the lipase activity inhibition ability thereof was measured. Particularly, when the lipase activity inhibition ability of a strain is excellent, the strain may inhibit the absorption of fat in the intestine, which is effective in preventing obesity. First, 14 strains having high lipase activity inhibition ability were first selected. Afterward, in order to select the strain with the best therapeutic and preventive effects of obesity among the 14 strains, an experiment to measure the lipase activity inhibition ability was performed using porcine pancreatic lipase (Sigma, USA). After diluting the sample to a concentration of 0.1 mg/mL, the diluted sample together with 0.167 mM p-nitrophenylpalmitate (PNP; Sigma, USA) solution, 0.061 M Tris-HCl buffer (pH 8.5) and 0.3 mg/mL lipase were input on a plate. Reaction occurred at 25° C. for 10 minutes. After the reaction, absorbance was measured at 405 nm. A control group in which the sample was replaced with a solvent was experimented. Then, the lipase inhibition activity was calculated based on the following equation. The measurement results are shown in Table 1.

Lipase inhibition activity (%)={1−(absorbance of sample/absorbance of control)}×100

TABLE 1

| Strains | Anti-lipase activity (%) |
|---|---|
| MG4227 | 12.24 |
| MG4231 | 12.24 |
| MG4244 | 11.22 |
| MG4261 | 10.53 |
| MG4270 | 11.84 |
| MG5008 | 10.53 |
| MG5013 | 12.24 |
| MG5029 | 11.84 |
| MG5033 | 10.53 |
| MG5040 | 10.53 |
| MG5055 | 10.53 |
| MG5087 | 11.84 |
| MG5098 | 14.47 |
| MG5105 | 11.84 |

As shown in the Table 1, it was identified that levels of the lipase inhibition activity of MG4227, MG4231, and MG4244 among the strains were higher. Therefore, it was found that the lipase inhibition activity of the four strains was greater than 10%, thereby to inhibit the absorption of fat in the intestine, and thus, the four strains have excellent treatment and prevention effect of the obesity.

2.2 Identification of Strains Having Inhibition Ability of Preadipocyte Differentiation In order to select a strain having excellent obesity prevention and treatment effects among the strains obtained in the Example 1, an experiment was conducted to identify the ability thereof to inhibit differentiation of preadipocytes into adipocytes. To induce the differentiation of 3T3-L1 preadipocytes, the preadipocytes were dispensed into each 96-well plate at $1.25 \times 10^5$ cells/well. After 2 days, the medium was changed so that the cells were completely fused on the 4th day. MDI (0.5 mM 3-isobutyl-1-methylxanthine), 1 μM dexamethasone and 1 μg/mL of insulin solution added to 10% FBS DMEM medium. Subsequently, in the experimental group, the culture supernatant of the strain obtained in Example 1 was added to the medium at a concentration of 1,000 μg/mL. 100 μM baicalin known to have excellent adipogenesis inhibition as a positive control was added thereto to induce differentiation. Adipocyte differentiation was completed after 6 days, and the amount of lipid accumulated in the cell was measured using Oil Red 0 (Sigma, USA), which reacts specifically with the lipid drop generated in the cell. After adipogenesis was terminated, the medium was removed and washing was carried out twice with PBS. The cells were fixed at 4° C. for 1 hour with 10% formalin. The fixed cells were washed twice with 60% isopropanol (in PBS) and stained with 0.5% Oil Red O solution for 30 minutes at room temperature. After the staining, the staining solution was removed and washing occurred twice with distilled water. For quantification, distilled water was removed, isopropyl alcohol was added to a completely dry well, and then, absorbance was measured at 520 nm. Then, a degree of inhibition of adipocyte differentiation ability was analyzed by comparing the produced lipid drop content with that of the MDI treatment group based on the measured absorbance. The analysis results are shown in Table 2.

TABLE 2

| Strains | Lipid accumulation (% of control) |
|---------|-----------------------------------|
| MG4227  | 84.46 |
| MG4231  | 80.04 |
| MG4244  | 71.90 |
| MG4261  | 75.52 |
| MG4270  | 73.14 |
| MG5008  | 83.15 |
| MG5013  | 81.50 |
| MG5029  | 83.45 |
| MG5033  | 77.02 |
| MG5040  | 82.94 |
| MG5055  | 75.56 |
| MG5087  | 78.74 |
| MG5098  | 80.71 |
| MG5105  | 82.18 |

As shown in Table 2, among the 14 types of lactic acid strains, MG4244 had the highest ability to inhibit adipocyte differentiation at 71.90%. MG4270, MG4261, MG5055, MG5033, MG5087 and MG4231 exhibited a relative lipid content of 81.40% or smaller. Thus, it was identified that the differentiation from preadipocytes to adipocytes was effectively inhibited when the 7 kinds of lactic acid bacteria were used. Particularly, considering that the relative lipid content was 81.40% in the positive control group (baicalin-treated group), it was identified that the above-disclosed seven strains exhibited a lower lipid content than 81.40%, thus achieving excellent inhibition of adipocyte differentiation ability.

2.3 Identification of Strains without Cytotoxicity

In order to select a strain without cytotoxicity while having excellent obesity prevention and treatment effects among the strains as obtained in the Example 1, in the Example 2.1 and 2.2, MTT (3-(4,5-dimethylthiazol-2-yl)-2,5-diphenyltetrazolium bromide) assay was performed to determine whether the 14 strains having excellent obesity prevention and treatment effects exhibit cytotoxicity to 3T3-L1 cells. The 3T3-L1 cells used in the experiment were purchased from the American Type Culture Collection (ATCC, MD, USA). The cells were cultured in Dulbecco's modified Eagle's medium (DMEM, Invitrogen, NY) containing 10% fetal bovine serum (FBS, Invitrogen, NY, USA) and 1% penicillin-streptomycin (Gibco, NY, USA) at 37° C. under a condition in which 5% $CO_2$/95% air was supplied. The 3T3-L1 cells cultured under the conditions were dispensed into a 96-well plate at a concentration of $16 \times 10^4$ cells/well. After incubation of the cells for 24 hours, the medium was removed. Thereafter, each sample diluted into 1,000 μg/mL was added to 1004 of new DMEM medium and incubated for 24 hours, and then 200 μL of an MTT (Sigma, USA) solution at 5 mg/mL was added thereto. The cells were incubated at 37° C. for 4 hours. The supernatant was removed after the incubation. After 200 μL of dimethyl sulfoxide (DMSO) was added thereto, absorbance was measured at 546 nm using a microplate reader (Bio-Rad Model 550; Hercules, Calif., USA) to determine whether the 14 strains were cytotoxic. The analysis results are shown in Table 3.

TABLE 3

| Strains | MTT assay (1,000 μg/mL) |
|---------|-------------------------|
| MG4227  | 92.52 |
| MG4231  | 99.63 |
| MG4244  | 108.42 |
| MG4261  | 98.85 |
| MG4270  | 88.60 |
| MG5008  | 80.49 |
| MG5013  | 97.00 |
| MG5029  | 88.07 |
| MG5033  | 92.75 |
| MG5040  | 81.15 |
| MG5055  | 84.06 |
| MG5087  | 96.32 |
| MG5098  | 88.07 |
| MG5105  | 82.28 |

As shown in the Table 3, it was identified that in all 14 types of lactic acid strains, the MTT assay results were 80 or higher. Thus, the treatment thereof at a concentration of 1,000 μg/mL did not affect the survival of cells, so that the 14 types of lactic acid strains had no cytotoxicity. As a result, the lactic acid strains which exhibit excellent obesity inhibition ability has no cytotoxicity, and thus may be highly useful for various purposes.

Example 3. Identification of Strains Having Obesity Prevention and Treatment Effects Among the strains having excellent obesity prevention and treatment effects as identified in the Example 2, the strains MG4231 and MG4244, both of which inhibit lipase enzyme activity and inhibit preadipocyte differentiation were selected as strains having obesity prevention and treatment effects. An experiment to identify the strains was performed. After incubating the selected strains at 37° C. for 24 hours in MRS liquid medium, Gram staining was performed and morphological characteristics thereof were observed with a phase contrast microscope. 16S rRNA gene sequencing was performed to identify the selected lactic acid strains, and the universal rRNA gene primers (27F and 1492R) were used for gene amplification. Each process was conducted by Sol-Gent Co. (Daejeon, Korea). The 16S rRNA sequencing results as analyzed were compared with the Genbank database via Basic Local Alignment Search Tool (BLAST) analysis (http://blast.ncbi.nlm.nih.gov/Blast.cgi) of the National Center for Biotechnology Institute (NCBI). Sequence was aligned via PHYDIT 3.1. Then, a phylogenetic tree was created using a neighbor joining method using MEGA 5.1 software. The results of identifying the two kinds of strains are summarized in Table 4.

TABLE 4

| Isolates | Strain | Homologous microorganism |
|----------|--------|--------------------------|
| Human vagina | MG4231 | Lactobacillus fermentum |
|  | MG4244 | Lactobacillus fermentum |

As identified in the Table 4, MG4231 and MG4244 were identified as Lactobacillus fermentum.

Example 4. Identification of Resistance of Selected Strains to Acid and Bile

In order for the lactic acid strains to be used as probiotics, resistance thereof to acid and bile is important. Thus, an experiment was performed to determine the resistance to acid and bile of Lactobacillus fermentum MG4231 and MG4244 at low pH (pH 2.0 to 4.0) and bile. Experiments were conducted by Maragkoudakis' method to identify the resistance of lactic acid strains to artificial gastric acid and artificial bile same as those in the intestinal environment. After incubating the selected lactic acid strains for 18 hours, the strains were centrifuged for 5 minutes at 2,000×g at 4° C. and washed twice with PBS, and then were suspended at a concentration of $10^8$ CFU/mL and used for resistance experiments. In order to identify the resistance thereof to artificial gastric acid, pepsin (Sigma-Aldrich, USA) was added to PBS (pH 2, 3, 4) so that the final concentration of pepsin (Sigma-Aldrich, USA) was 3 g/L, and then the lactic acid bacteria suspension was added thereto. After incubation for 3 hours at 37° C., the number of viable cells was identified. Artificial bile resistance was measured as follows. Pancreatin (Sigma-Aldrich, USA) was added to PBS (pH 7, 8) so that the final concentration of pancreatin (Sigma-Aldrich, USA) was 1 g/L, and then the suspension of lactic acid bacteria was added thereto and incubated at 37° C. for 4 hours. Then, we identified the number of viable cells. The results of the acid resistance test of the selected strains are shown in FIG. 1, and the results of the bile resistance test thereof are shown in FIG. 2.

Figure 1:
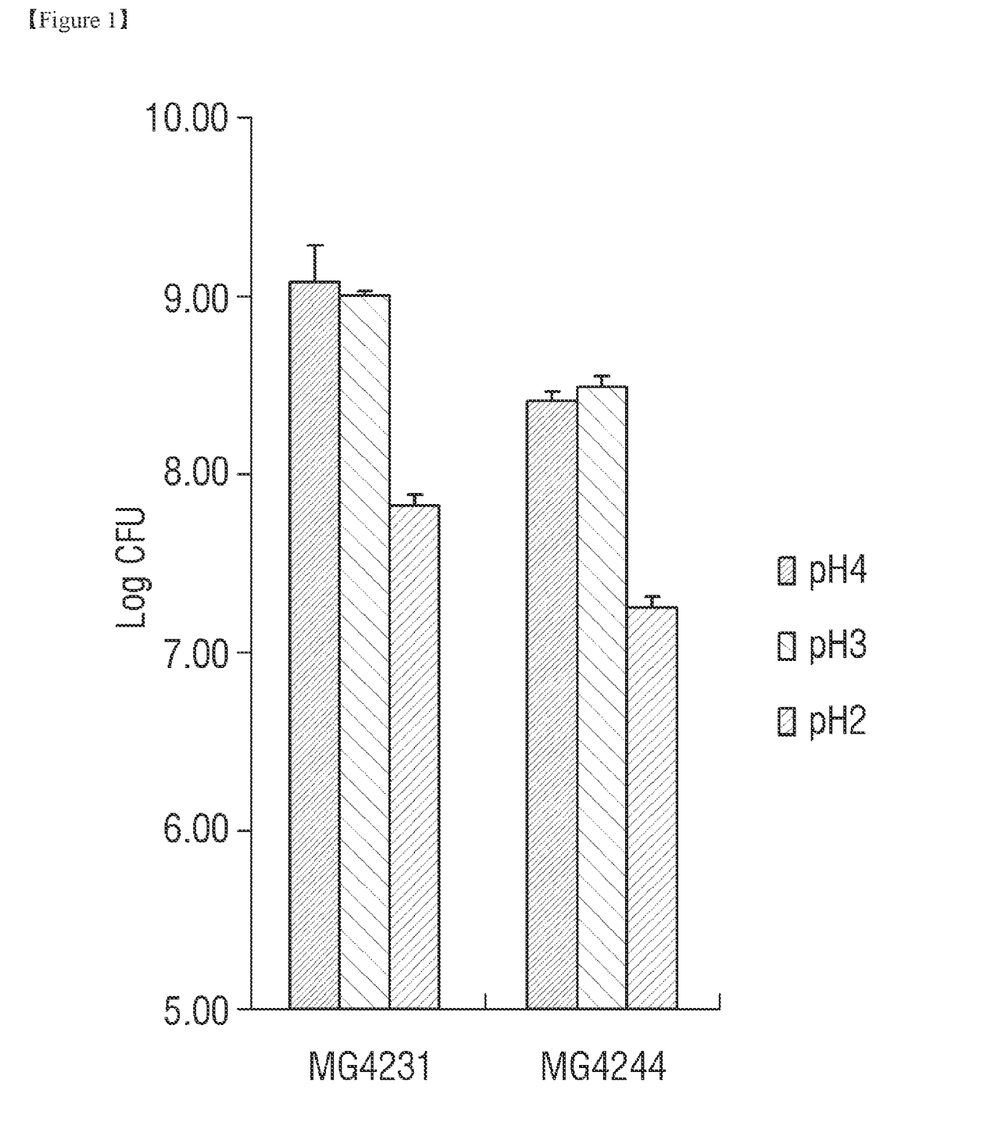
FIG. 1 is a diagram showing the results of a viability experiment of *Lactobacillus fermentum* MG4231 strain or MG4244 strain in a gastric fluid environment at pH 2 to 4 to determine the viability of the *Lactobacillus fermentum* MG4231 strain or MG4244 strain in the gastrointestinal environment.

As shown in FIG. 1, it was identified that MG4231 and MG4244 maintained a high viability with almost no decrease in the viability of the strain even at pH 3 to 4, which is a strong acid condition containing pepsin in the acid resistance experiment. In particular, it was identified that even under pH 2 condition, there was no rapid decrease in viability, compared to the viability at pH 3 to 4, and thus, both strains exhibited an excellent degree of acid resistance without a sudden decrease in strain viability at pH 2 to 4.

Figure 2:
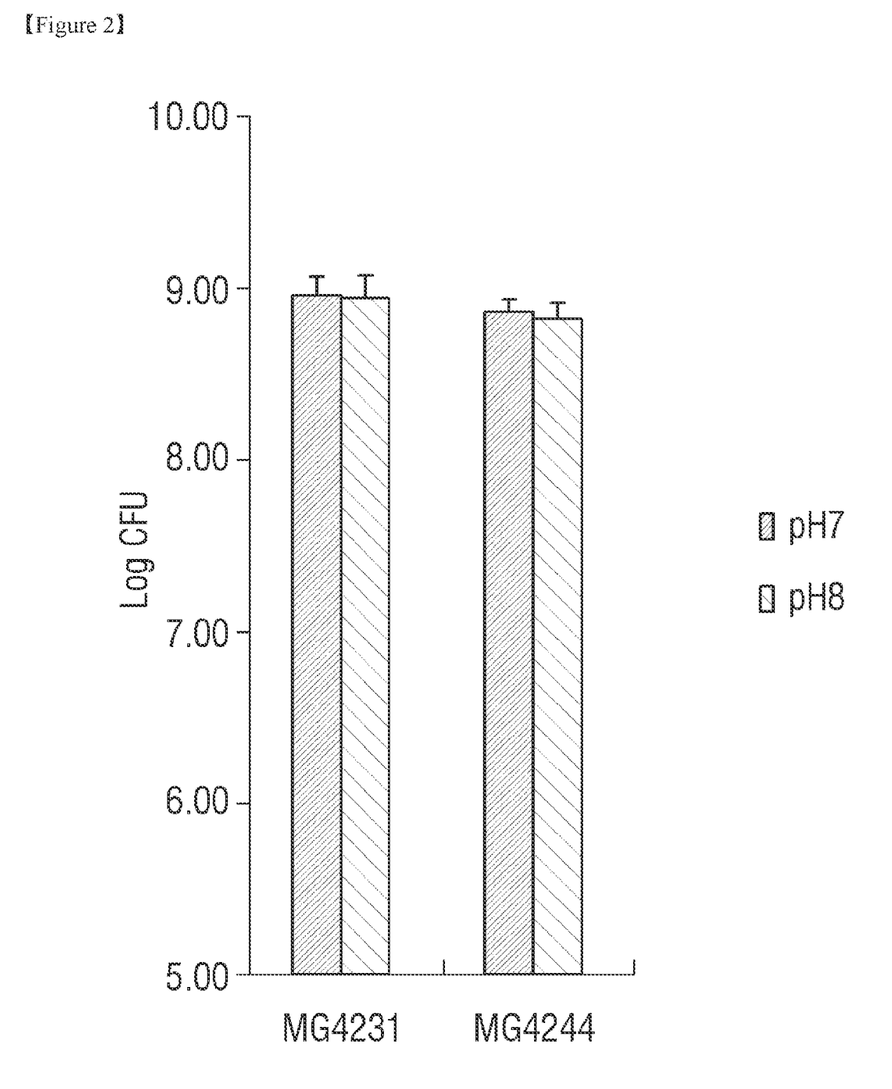
FIG. 2 is a diagram showing the results of a viability test of *Lactobacillus fermentum* MG4231 strain or MG4244 strain in the intestinal environment at pH 7 and 8 to identify the viability of the *Lactobacillus fermentum* MG4231 strain or MG4244 strain in bile environment.

As shown in FIG. 2, it was also identified that there was little reduction in the viability of MG4231 and MG4244 in the bile containing pancreatin at pH7 and pH8.

In conclusion, it was identified that Lactobacillus fermentum MG4231 and MG4244 have high resistance to low pH and to bile, which is one of the most important requirements as probiotics.

Example 5. Identification of Auto-Aggregation Ability of Selected Lactic Acid Strains When the auto-aggregation ability of the strain is good, the strain is useful as probiotics because the ability prevents the removal of probiotics by intestinal spasm and effectively allows formation of colonies in the epithelial cells of the digestive tract in the intestine. An experiment was performed to identify the auto-aggregation ability of the selected Lactobacillus fermentum MG4231 and MG4244. After incubating the selected lactic acid strain at 37° C. for 18 hours, centrifugation was performed at 4,000×g at 4° C. for 5 minutes, and then the strains were washed twice with PBS. After resuspending the strains so that the final concentration of the suspension became OD600 of 1.0, 5 mL of the suspension was shaken for 10 seconds and left for 5 hours to identify auto-aggregation ability. Immediately after the start of the experiment (A0) and 5 hours later (A), 0.1 mL of the supernatant was taken, mixed with 0.9 mL of PBS, respectively. Then, the absorbance was measured at 600 nm (A0, A). The auto-aggregation ability was calculated according to the following calculation formula. The result of this identification is shown in FIG. 3.

$$\text{Auto-aggregation ability (\%)} = (A0-A)/A0 \times 100$$

Figure 3:
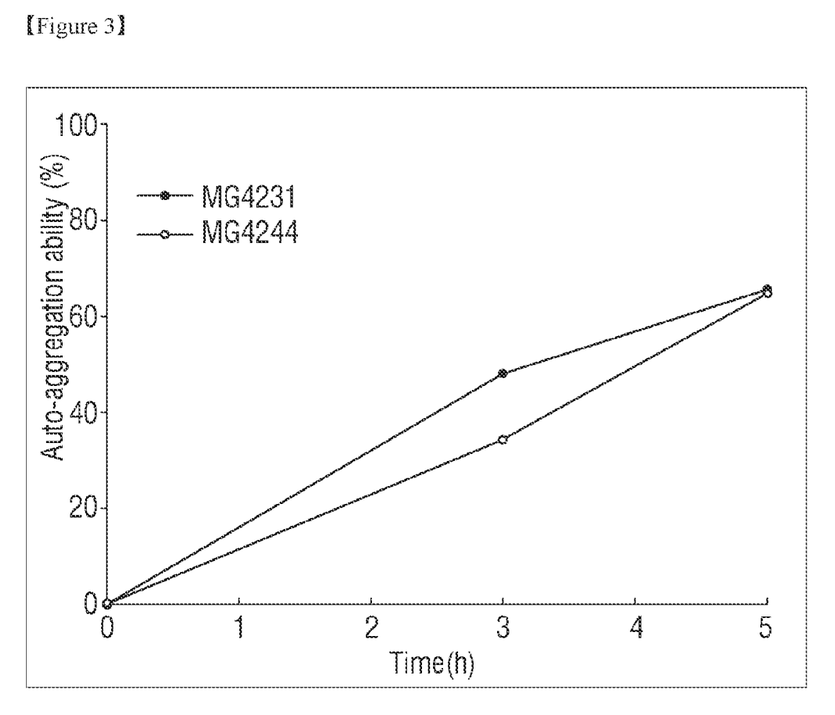
FIG. 3 is a diagram showing the experimental results of identifying the auto-aggregation ability of *Lactobacillus fermentum* MG4231 strain or MG4244 strain.

As shown in FIG. 3, it was identified that the auto-aggregation ability of Lactobacillus fermentum MG4231 measured 5 hours after the experiment was 65.3±0.9%. The auto-aggregation ability of Lactobacillus fermentum MG4244 was identified as 68.6±0.9%. Thus, it was identified that both the strains may act as an effective probiotic due to the high self-aggregation ability.

Example 6. Identification of Ability of Selected Lactic Acid Strains to Inhibit Triglyceride Accumulation An experiment was performed to identify whether the selected strains, Lactobacillus fermentum MG4231 and MG4244 may inhibit the accumulation of triglyceride. Lactobacillus fermentum MG4231 and MG4244 strains were cultured, centrifuged, and lyophilized. 10 mg of the lyophilized powder strain ($1 \times 10^8$ CFU) was quantified, dissolved in 1 ml of distilled water, and filtered. The group that was not treated with anything was used as a control group. A first group was treated only with MDI (0.5 mM 3-isobutyl-1-methylxanthine) that may activate adipogenesis. In a second group, differentiated 3T3-L1 adipocyte was treated with MDI, and 50 µl and 100 µl of the filtered strain (LFS). A TG assay on the control, and the first and second groups was performed to measure an amount of triglyceride thereof. Then, the measured results of the three groups were compared with each other to analyze the degree of triglyceride inhibition. The analysis results are shown in FIG. 4.

Figure 4:
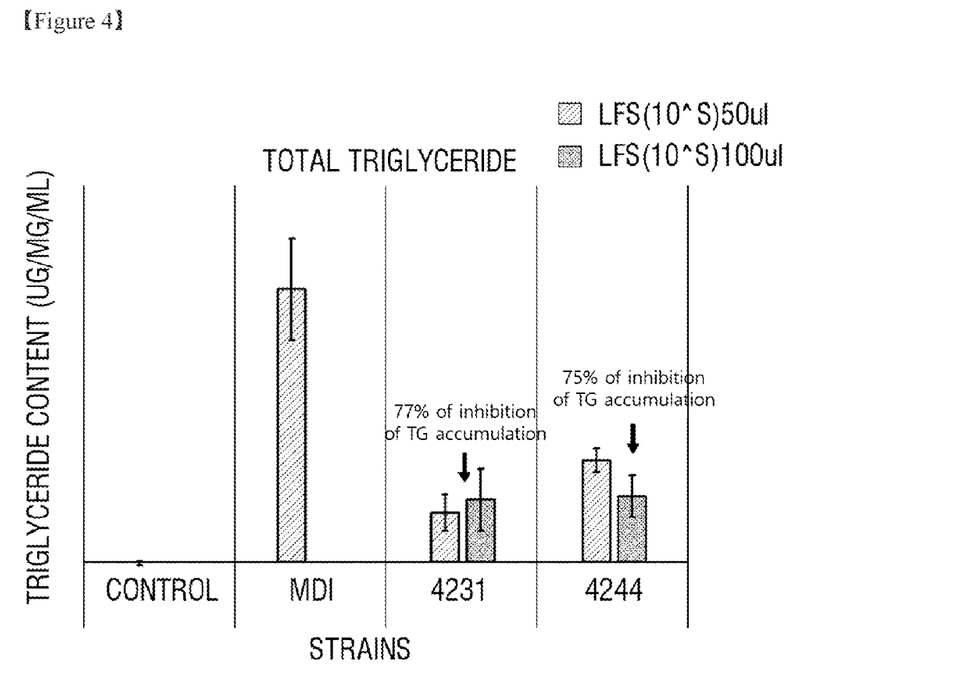
FIG. 4 is a diagram showing the results of an experiment to identify the effect of triglyceride accumulation inhibition of *Lactobacillus fermentum* MG4231 strain or MG4244 strain.

As shown in FIG. 4, about 77% of inhibition of triglyceride accumulation was identified in Lactobacillus fermentum MG4231, compared to the MDI-treated group. Further, in Lactobacillus fermentum MG4244, about 75% of triglyceride accumulation inhibition was identified. In particular, it is generally known that when the triglyceride accumulation is inhibited by 50% or more, it is generally recognized that the triglyceride accumulation inhibition effect is excellent. Thus, Lactobacillus fermentum MG4231 and MG4244 have excellent triglyceride accumulation inhibition effects.

[Accession Number]

Name of the deposit institution: Korea Research Institute of Bioscience and Biotechnology, 181 Ipsin-gil, Jeongeup-si., Jeollabuk-do56212, Republic of Korea Accession number: KCTC13593BP Deposition Date: Jul. 20, 2018

Name of the deposit institution: Korea Research Institute of Bioscience and Biotechnology, 181 Ipsin-gil, Jeongeup-si., Jeollabuk-do56212, Republic of Korea Accession number: KCTC13594BP Deposition Date: Jul. 20, 2018

The invention claimed is:

1. A method for alleviation, prevention or treatment of obesity or obesity-related diseases, comprising administering a composition comprising a Lactobacillus fermentum MG4244 (deposit number: KCTC 13594BP) or a culture medium comprising the strain to a subject in need thereof, wherein the strain inhibits lipase enzyme activity, preadipocyte differentiation activity, or triglyceride accumulation activity.

2. The method of claim 1, wherein the composition is a pharmaceutical composition, food composition, or health functional food composition.

3. The method of claim 1, wherein the strain has acid resistance, bile resistance, and auto-aggregation ability.

4. The method of claim 1, wherein the strain derived from an inner wall of a vagina.

5. The method of claim 1, wherein the obesity-related disease includes at least one selected from the group consisting of flirty liver, type 2 diabetes, hyperlipidemia, cardiovascular disease, arteriosclerosis, and lipid-related metabolic syndrome.

6. The method of claim 1, wherein the composition further comprises a pharmaceutically acceptable earlier, excipient or diluent.

* * * * *

UNITED STATES PATENT AND TRADEMARK OFFICE
CERTIFICATE OF CORRECTION

PATENT NO. : 11,484,557 B2
APPLICATION NO. : 17/271076
DATED : November 1, 2022
INVENTOR(S) : Paek et al.

It is certified that error appears in the above-identified patent and that said Letters Patent is hereby corrected as shown below:

In the Specification

Column 11, Line 62: Please correct "1004" to read --100 µL--

Column 11, Line 63: Please correct "200 µL" to read --20 µL--

In the Claims

Column 15, Line 7, Claim 5: Please correct "flirty liver" to read --fatty liver--

Column 15, Line 11, Claim 6: Please correct "earlier" to read --carrier--

Signed and Sealed this
Twenty-first Day of February, 2023

Katherine Kelly Vidal
*Director of the United States Patent and Trademark Office*